(12) United States Patent
Cutrer

(10) Patent No.: US 9,498,644 B2
(45) Date of Patent: Nov. 22, 2016

(54) APPARATUS FOR BRACHYTHERAPY

(71) Applicant: BEST MEDICAL INTERNATIONAL, INC., Springfield, VA (US)

(72) Inventor: Lloyd Michael Cutrer, Huntington Beach, CA (US)

(73) Assignee: Best Medical International, Inc., Springfield, VA (US)

( * ) Notice: Subject to any disclaimer, the term of this patent is extended or adjusted under 35 U.S.C. 154(b) by 0 days.

(21) Appl. No.: 14/795,730

(22) Filed: Jul. 9, 2015

(65) Prior Publication Data

US 2015/0306422 A1    Oct. 29, 2015

Related U.S. Application Data

(63) Continuation-in-part of application No. 12/983,429, filed on Jan. 3, 2011, now Pat. No. 9,283,402.

(51) Int. Cl.
*A61N 5/00* (2006.01)
*A61N 5/10* (2006.01)
(Continued)

(52) U.S. Cl.
CPC ........ *A61N 5/1015* (2013.01); *A61M 25/1011* (2013.01); *A61B 2018/00285* (2013.01); *A61M 2025/1013* (2013.01)

(58) Field of Classification Search
CPC ............... A61N 5/1015; A61N 2005/1018; A61N 2005/1005; A61N 2005/1021; A61M 2210/0687; A61M 2230/005; A61M 2025/1013; A61M 2025/1075; A61M 25/1011
USPC ........ 600/3, 7, 1, 2, 8, 564, 567, 6, 104, 15, 600/19, 41, 431, 562, 563, 566, 568, 9; 604/101.02, 103.02, 104, 164.01, 604/164.08, 309, 35, 43, 45, 523, 540, 57, 604/912, 913, 915, 96.01; 128/897–899
See application file for complete search history.

(56) References Cited

U.S. PATENT DOCUMENTS

| 5,653,683 A | 8/1997 | D'Andrea |
| 5,720,717 A | 2/1998 | D'Andrea |
| 5,913,813 A * | 6/1999 | Williams ............. A61N 5/1015 600/3 |

(Continued)

OTHER PUBLICATIONS

"Hologic takes SenoRx assets in out-of-court settlement with C.R. Bard", A. Sarvestani, www.massdevice.com, Aug. 14, 2013 (downloaded, Oct. 19, 2015), 4 pages.

(Continued)

*Primary Examiner* — Navin Natnithithadha
*Assistant Examiner* — Sunita Reddy

(57) ABSTRACT

A double-balloon brachytherapy catheter includes an outer-balloon that is filled with a liquid substance or air via an outer-balloon-filler. Further, an inner-balloon is filled with a liquid substance or air via an inner-balloon-filler, with the inner-balloon inserted inside the outer-balloon. Additionally, a plurality of radiation-tubes is positioned in association within the inner-balloon, such as to an outside border of the inner-balloon and within the outer-balloon. Each radiation-tube out of the plurality is segmented into segments of differing hardness. In addition, a vacuum-tube can be wrapped around an exterior of the outer-balloon, where the vacuum tube is used to remove fluids and air to create a void. Also, the plurality of radiation-tubes can be configured to run longitudinally along a central shaft of the double-balloon brachytherapy catheter.

21 Claims, 10 Drawing Sheets

(51) Int. Cl.
*A61M 25/10* (2013.01)
*A61B 18/00* (2006.01)

(56) References Cited

U.S. PATENT DOCUMENTS

| | | |
|---|---|---|
| 6,616,629 B1 | 9/2003 | Verin et al. |
| 6,923,754 B2 | 8/2005 | Lubock |
| 6,955,641 B2 | 10/2005 | Lubock |
| 7,357,770 B1 | 4/2008 | Cutrer et al. |
| 8,251,884 B2 | 8/2012 | Lubock et al. |
| 8,277,370 B2 | 10/2012 | Quick |
| 8,287,442 B2 | 10/2012 | Quick |
| 8,348,825 B2 | 1/2013 | Partridge et al. |
| 8,360,950 B2 | 1/2013 | Acosta et al. |
| 8,568,284 B2 | 10/2013 | White et al. |
| 9,283,402 B2 | 3/2016 | Cutrer |
| 2004/0087827 A1 | 5/2004 | Lubock |
| 2008/0221384 A1* | 9/2008 | Chi Sing .............. A61N 5/1015 600/7 |
| 2009/0143634 A1* | 6/2009 | Benson ................ A61N 5/1015 600/3 |
| 2009/0198095 A1* | 8/2009 | Acosta ............. A61M 25/1036 600/3 |
| 2009/0264696 A1* | 10/2009 | White .................. A61N 5/1015 600/8 |
| 2009/0312593 A1* | 12/2009 | Drobnik .............. A61N 5/1015 600/3 |

OTHER PUBLICATIONS

"Best Dual Balloon Breast Brachytherapy Applicator", from TeamBest brochure/material, Sep. 13, 2014, 3 pages.

* cited by examiner

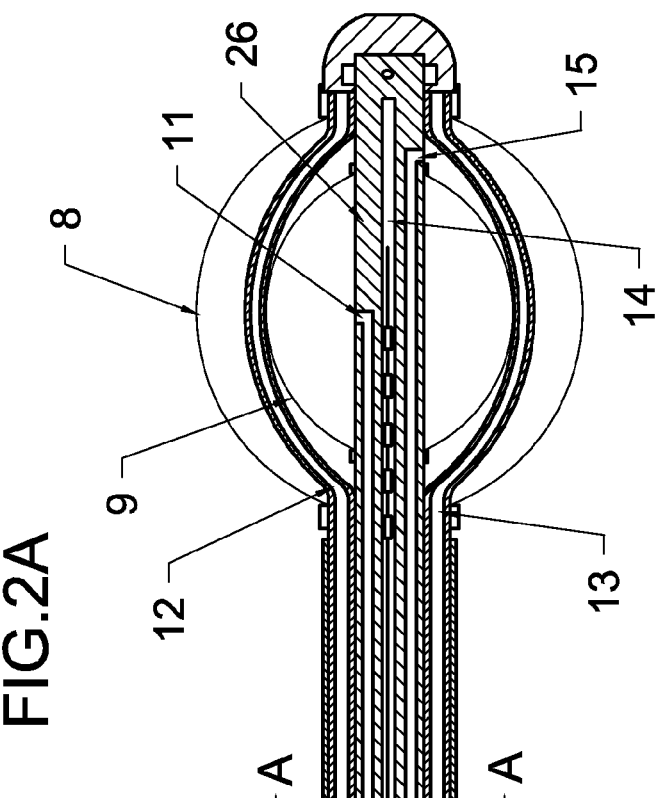
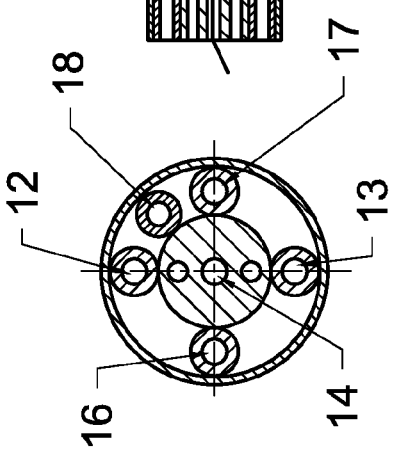

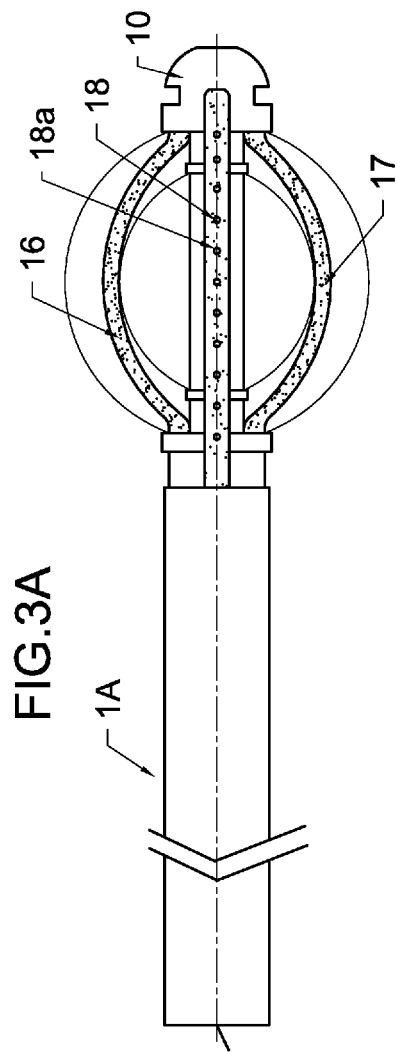
FIG.3A
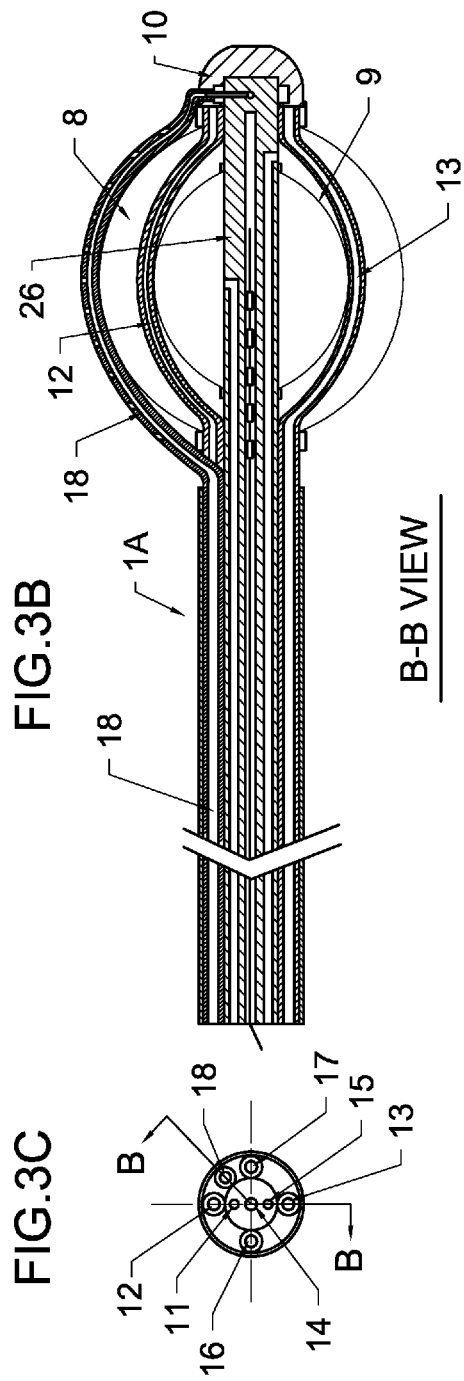
FIG.3B
B-B VIEW
FIG.3C

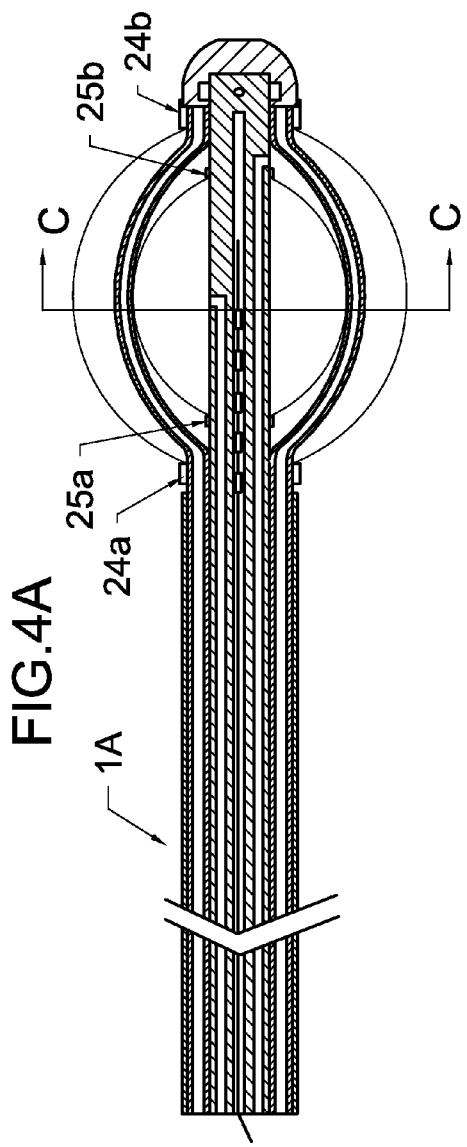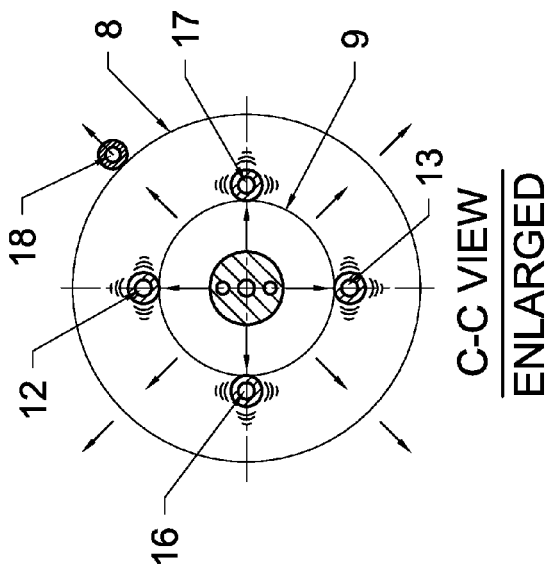

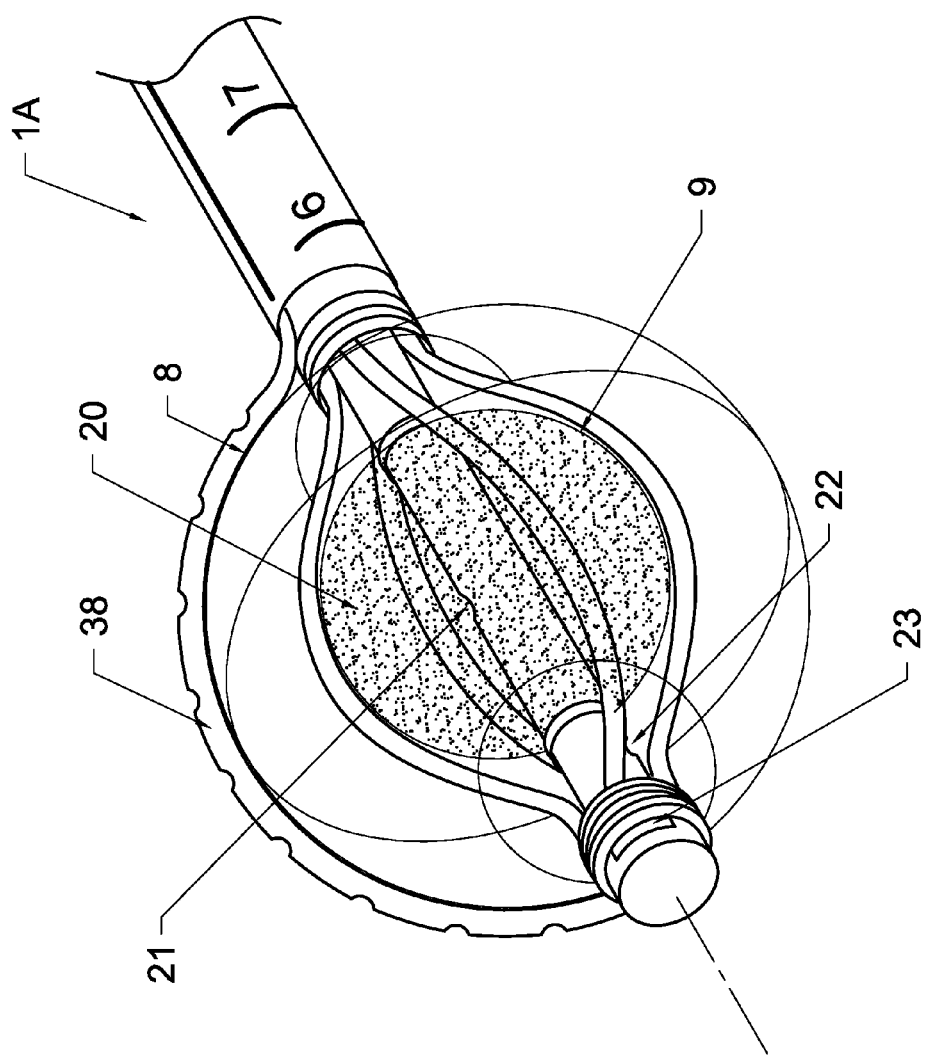

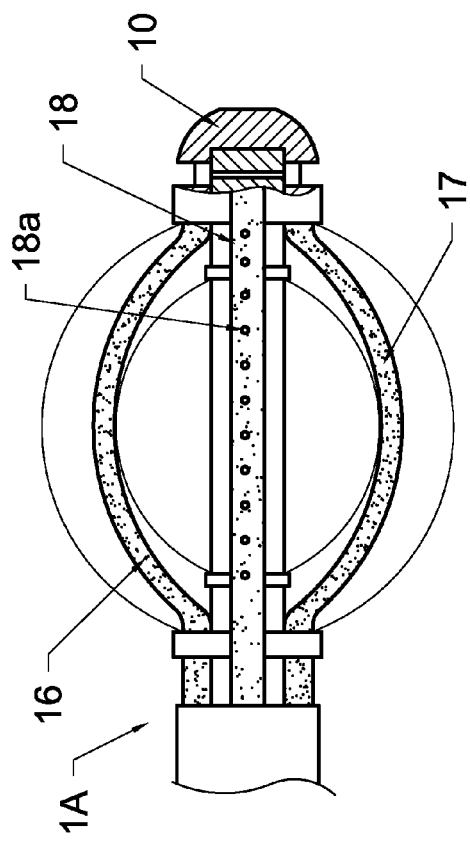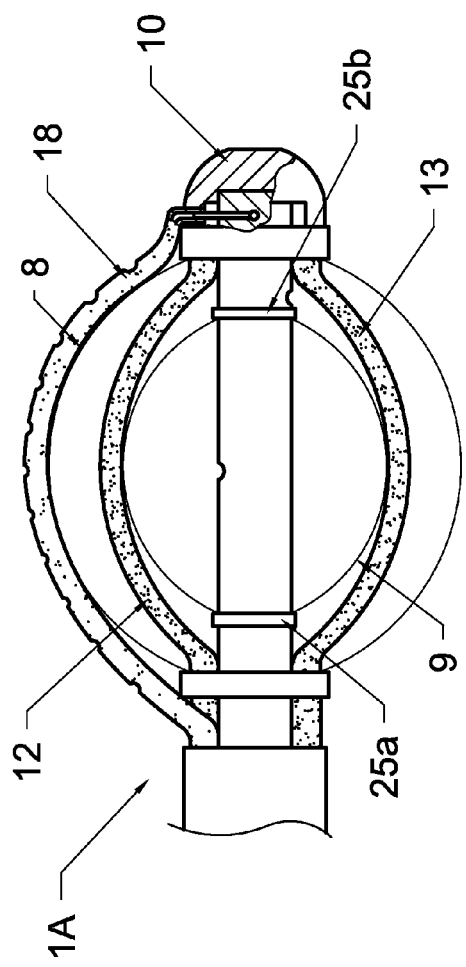

APPARATUS FOR BRACHYTHERAPY

CROSS REFERENCE TO RELATED APPLICATION

This application is a continuation-in-part of U.S. application Ser. No. 12/983,429, filed Jan. 3, 2011, and claims benefit thereto and is incorporated herein by reference in its entirety.

BACKGROUND OF THE INVENTION

1. Field of the Invention

The invention generally relates to a device that allows for a conformal radiation dose distribution by allowing medical personnel to change the position and angle of a radiation source by inflating two balloons, whereby an inner-balloon positions treatment catheters within an outer-balloon.

2. Description of Related Art

In diagnosing and treating malignant tumors, medical physicians all over the world have tried to create innovative devices designed to treat cancerous tumors. At one time cancer could only be diagnosed when a tumor was big enough to see or feel. Now sophisticated imaging systems can identify tumors far earlier, often before any symptoms have even appeared, thereby allowing for early treatment and potential cure. Over the years many different methods have been developed to treat cancer. For breast cancer, surgical approaches such as radical mastectomies were used to remove the breast, chest muscles and underarm lymph nodes. These procedures were occasionally performed as early as the 19th century. The late 1940s brought the modified radical mastectomy, which spared the muscle tissue of the patient. In the 1970s, a more limited surgical option came into use, known as Breast Conservation Surgery, which focused on removal of the tumor and a small amount of surrounding tissue commonly referred to as a lumpectomy. In 1985, the lumpectomy combined with whole breast radiation therapy was found to be as effective as the mastectomy in terms of survival rates, but resulted in higher local relapse rates. As a result, medical research looked to provide other forms of combined surgical and localized radiation treatment options.

Beginning in the 20th century, shortly after radiation began to be used for diagnosis and therapy, it was discovered that radiation could cause cancer as well as cure it. Many early radiologists used the skin of their arms to test the strength of radiation from their radiotherapy machines. These radiologists looked for a dose that would produce a pink reaction, referred to as an erythema, which looked like sunburn. They called this the "erythema dose," and this was considered an estimate of the proper daily fraction of radiation. In retrospect, it is no surprise that many developed leukemia.

Today, a lumpectomy is a common surgical procedure designed to remove a discrete lump, usually a benign or malignant tumor from an affected woman's breast, or in rare occasions, a man's breast. As the tissue removed is generally quite limited and the procedure relatively non-invasive, compared to a mastectomy, a lumpectomy is considered a viable means of "breast conservation" or "breast preservation" surgery with all the attendant physical and emotional advantages of such an approach.

In the past, a few breast balloon brachytherapy devices have been developed. The most common types available are the Contura® multi-lumen balloon breast brachytherapy device, and the MammoSite® breast brachytherapy device. Both devices are used in a procedure known as Accelerated Partial Breast Irradiation. These devices can have certain drawbacks which will be described in detail below.

An example of a brachytherapy applicator is the "MammoSite® Radiation Therapy System (RTS)," developed by Proxima Therapeutics, Inc., Alpharetta, Ga. 30005 USA. The MammoSite® RTS, a balloon catheter which is used in a high dose rate radiation procedure, was introduced specially for use in partial breast irradiation. The MammoSite® catheter is inserted at the time of a lumpectomy or within 30 days following surgery, remains in place during treatment, and is deflated and removed at the end of treatment, typically with a patient receiving a mild pain medication. A solid radiation source is typically used. However, a liquid radiation source can also be used with a balloon device placed within a body cavity, such as exhibited in Iotrex®, by Proxima Therapeutics, Inc. The solid radiation source can be removed following each treatment session, while the liquid radiation source typically remains in place as long as the balloon remains within the body cavity.

Clinical trials have shown the efficacy of inflatable treatment delivery devices and systems, such as the MammoSite® RTS and similar devices and systems. For example, such systems can include systems offered by GliaSite® RTS and Proxima Therapeutics, Inc. However, radiation treatment delivered via these devices and systems can have an effect on healthy tissue, while providing a desired effect on cancerous tissue, and, as such, can have a limited dose optimization, and can be attributed to their design. In a radiation treatment, care must be taken to direct the maximum therapeutic dose to diseased tissue while minimizing radiation dose to healthy tissue. For example, radiation treatment can be relatively most effective when substantially all surrounding tissue regions receive the same dose of radiation, and where the radiation dosage received by more distant tissue is as small and as uniform as possible. However, because tissue cavities typically are not uniform in their sizes or shapes and can be near critical structures, such as the skin, a lung, or the heart, radiation delivered via the aforementioned inflatable delivery devices can result in less than optimal dosages to different regions of surrounding tissue in that the treatment catheters of such known inflatable delivery devices are substantially limited in movement or are fixed in the device and, therefore, are fixed in the cavity. This can create regions referred to as "hot spots" and can also create regions of relatively low dosage referred to as "cold spots."

In addressing non-uniform cavities as can be present in a treatment of the surrounding tissue, various devices and systems have been developed to draw adjacent tissue near a treatment device. See, for example, U.S. Pat. No. 6,923,754 B2 to Lubock and U.S. Pat. No. 6,955,641 B2 to Lubock. The Lubock patents describe devices and systems that utilize a vacuum to draw tissue surrounding a body cavity towards a treatment device placed within the cavity. The Lubock devices add a sheath or a fluid-permeable enclosure wall and a vacuum conduit to the MammoSite® RTS or similar inflatable treatment delivery device. These added elements create suction around the device, which draws tissue against the device surface within a body cavity, as can allow a closer contact between the tissue and the device. Control over the distance, spacing, and the amount of tissue contact can offer some advantages to the treatment of a lining of a body cavity.

However, with such devices and systems, a relatively common shortcoming of these applicators is that the source typically can only travel in or near a central catheter or a centralized set of catheters within a cylindrical or spherical balloon applicator. Typically, the existing balloon catheters only allow an offset from the center shaft of approximately 0 mm to 5 mm, for example. Such designs can limit the ability to maximize dose conformality and homogeneity, which can only be maximized by allowing the treatment catheters to be placed significantly farther away from the central position. For example, after a surgery, doctors may find that the cavity wall is near sensitive regions which may have a higher sensitivity to radiation damage, including development of new cancerous tissue, than other areas surrounding the resection cavity. Doctors typically are always looking to deliver the maximum prescribed dose to the target region while minimizing dose to critical structures. Therefore, there is a need in the art to move the treatment catheters farther away from the central shaft of the balloon device to provide enhanced dose conformality, or dose shaping. This can allow for greater flexibility in dose delivery to both target structures, as well as those regions where reduced dose would be beneficial.

Design of intra-cavity applicators for brachytherapy can be a challenging process, as the bio-mechanical and radiation dosimetry properties of the applicators should desirably minimize the trauma to the patient during the applicator insertion process. Further, these applicators desirably should allow optimal radiation dose conformality to the tumor tissues. Finally, these applicators desirably should have adequate mechanical strength so that the location of the applicator can be predicted throughout a course of treatment. Developments in medical imaging, such as computerized axial tomography (CT), magnetic resonance imaging (MRI), and positron emission tomography (PET) imaging, have provided clinicians with various means to identify tumors on patient images at earlier stages with relatively increased confidence. However, as described, technical mechanisms to deliver an enhanced conformal dose can be limited by the available applicators. Therefore, it would be desirable to provide devices and systems for treatment that promote achieving an optimal radiation dose distribution to a variety of tumors in or near body cavities.

Thus, apparatuses and methods for addressing the aforementioned problems are desired.

SUMMARY OF THE INVENTION

Embodiments of a double-balloon brachytherapy catheter include an outer-balloon that is selectively filled to an outer balloon size with a liquid substance or air via an outer-balloon-filler, an inner-balloon that is selectively filled to an inner balloon size with a liquid substance or air via an inner-balloon-filler, wherein the inner-balloon is positioned inside the outer-balloon, and a plurality of radiation-tubes positioned in association with and moved into a corresponding radiation-delivery position by the inner-balloon, the plurality of radiation-tubes being segmented into segments of differing hardness to selectively expand or contract a length of one or more of the segments to correspond to the radiation delivery position, wherein the outer balloon size and the inner balloon size are mutually independent such that the outer balloon size and the inner balloon size are selectively adjusted independent of each other, and so that the plurality of radiation tubes are selectively adjustable to the corresponding radiation-delivery position by varying the inner balloon size to optimize radiation delivery for any size cavity.

In embodiments of a double-balloon brachytherapy catheter the inner-balloon-filler increases a volume of the inner-balloon to selectively expand or contract the length of one or more segments of the plurality of radiation-tubes to correspond to a change in an angle and a length or to a change in location and an angle of the plurality of radiation-tubes to optimize radiation delivery. This change in the angle and the length of the radiation-tubes facilitates reducing hot spots and cold spots in the radiation treatment. Embodiments of the double-balloon brachytherapy catheter can further include a vacuum-tube that is attached to the distal-tip of the double-balloon brachytherapy catheter or is positioned outside of the outer-balloon to allow for removal of fluids or air from around the distal-tip or from around the outside of the outer-balloon.

Additional features of embodiments of the double-balloon brachytherapy catheter can include that the segments of the plurality of radiation tubes include at least one segment having a lower durometer value than another segment. The segments can also include a biasing segment, such as a spring material to selectively adjust a length of a corresponding radiation tube. Also, the segments of differing hardness can be secured together by a securing mechanism, such as by a collar, for example.

Also, embodiments of methods for treating a patient by operating a double-balloon brachytherapy catheter include selectively filling a liquid substance or air into an outer-balloon via an outer-balloon-filler to achieve an outer balloon size, a plurality of radiation-tubes segmented into segments of differing hardness being positioned within the outer-balloon, selectively filling a liquid substance or air into an inner-balloon via an inner-balloon-filler to achieve an inner balloon size, the inner-balloon being positioned inside the outer-balloon, selectively expanding or contracting a length of one or more of the segments of a corresponding one or more of the plurality of radiation tubes to correspond to a radiation delivery position by selectively filling the inner-balloon via the inner-balloon-filler, and selectively controlling the outer balloon size and the inner balloon size independently of each other, wherein the plurality of radiation tubes are selectively adjustable to the radiation-delivery position by varying the inner balloon size to optimize radiation delivery for any size cavity.

Embodiments of methods for treating a patient by operating a double-balloon brachytherapy catheter can also include loading radioactive material into at least one of the plurality of radiation-tubes to provide a radiation dose treatment. Also, embodiments of methods can further include selectively increasing or decreasing a volume of the inner-balloon to selectively expand or contract the length of one or more segments of the plurality of radiation-tubes to correspond to a change in an angle and a length or to correspond to a change in a location and an angle of the plurality of radiation-tubes to optimize radiation delivery. Further, features of the methods can also include removing by a vacuum-tube fluids or air from a cavity receiving the double-balloon brachytherapy catheter.

These and other features of the present invention will become readily apparent upon further review of the following specification and drawings.

BRIEF DESCRIPTION OF THE DRAWINGS

FIG. 2A is a cross-sectional side view of an internal structure of a shaft in a double-balloon brachytherapy catheter according to the present invention.

FIG. 2B is a cross-sectional front view of an internal structure of a shaft in a double-balloon brachytherapy catheter according to the present invention.

FIG. 3A is a top view of a double-balloon brachytherapy catheter having a vacuum-tube according to the present invention.

FIG. 3B is a cross-sectional side view of a double-balloon brachytherapy catheter having a vacuum-tube according to the present invention.

FIG. 3C is a cross-sectional front view of a double-balloon brachytherapy catheter having a vacuum-tube according to the present invention.

FIG. 4A is a cross-sectional side view of an internal structure of a double-balloon brachytherapy catheter and flexible radiation dose tubes according to the present invention.

FIG. 4B is a cross-sectional front view of an internal structure of a double-balloon brachytherapy catheter and flexible radiation dose tubes according to the present invention.

FIG. 6 is a perspective view of an internal balloon fill volume of a double-balloon brachytherapy catheter having a vacuum-tube according to the present invention.

FIG. 7A is a sectional top view of a double-balloon brachytherapy catheter having a vacuum-tube according to the present invention.

FIG. 7B is a sectional side view of a double-balloon brachytherapy catheter having a vacuum-tube according to the present invention.

Unless otherwise indicated, similar reference characters denote corresponding features consistently throughout the attached drawings.

DETAILED DESCRIPTION OF THE INVENTION

Figure 1:
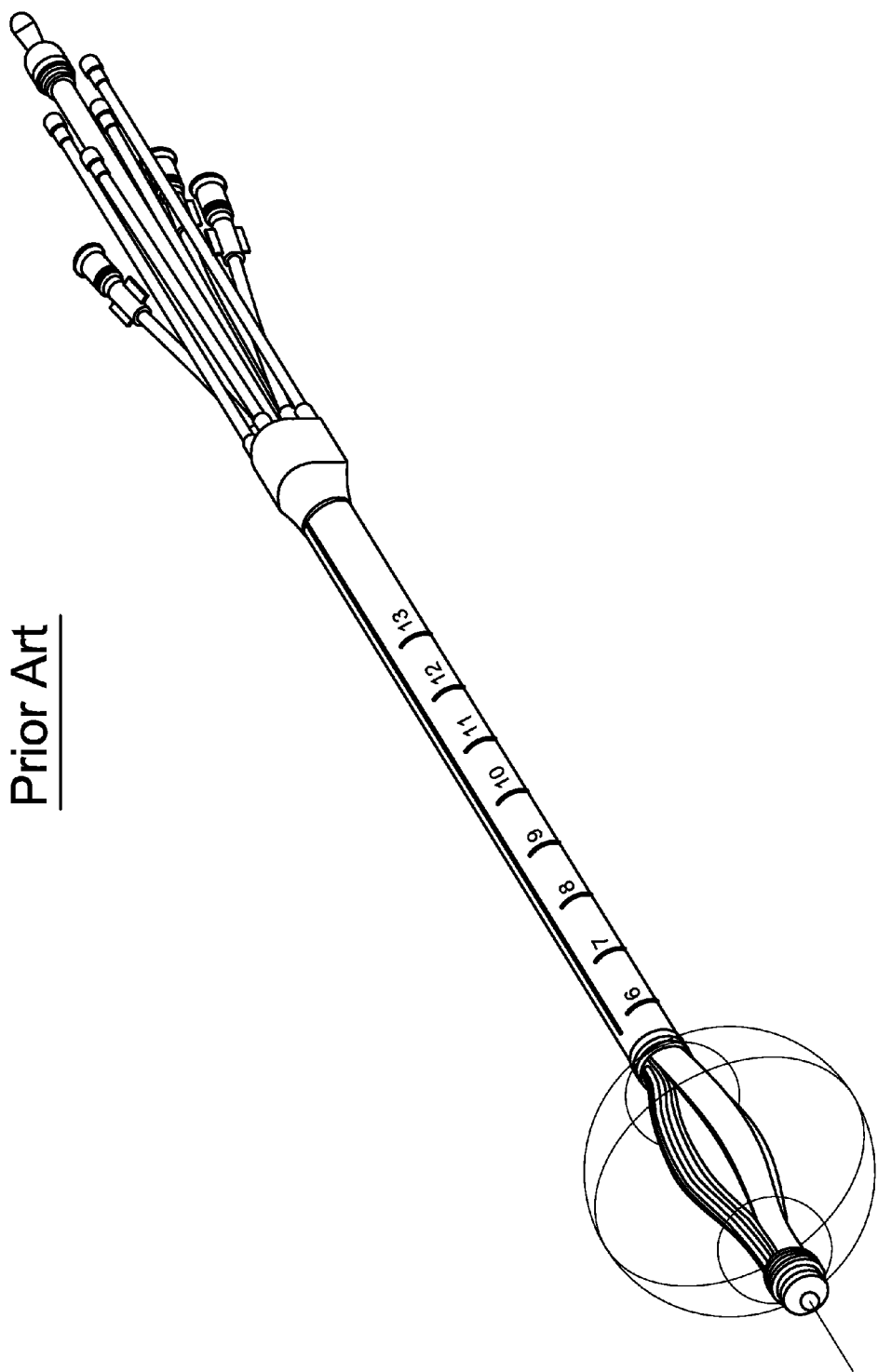
FIG. 1 is a perspective view of a prior art multi-lumen breast single balloon catheter with fixed treatment catheters.

The invention generally relates to devices and methods that allow for a conformal dose distribution to a patient by enabling medical personnel the ability to change the location and angle of a radiation source by inflating the balloons of the device. The devices and methods described herein can be applied to a patient undergoing treatment for a variety of reasons. For example, the devices and methods can be implemented to treat a patient having breast cancer, colon cancer, cervical cancer, and oral cancer, among other examples. Further, embodiments of the devices described herein can be implanted and inserted into a variety of regions of a patient's anatomy. For example, embodiments of the devices can be used in conjunction with a patient's mouth, breast, and rectum, among other examples.

The following detailed description is provided to assist in providing an understanding of embodiments of methods, apparatuses/devices, and/or systems described herein. Accordingly, various changes, modifications, and equivalents of the systems, apparatuses and/or methods described herein can be made within the scope of the disclosure. Also, descriptions of well-known functions and constructions may be omitted for increased clarity and conciseness.

Referring now to FIGS. 2-7, a double-balloon brachytherapy catheter 1A is shown. FIG. 2A shows a double-balloon brachytherapy catheter 1A without a suction/vacuum-tube 18. The double-balloon of the double-balloon brachytherapy catheter 1A can allow for medical personnel to provide an optimized dose distribution to a region of interest. The double-balloon structure can include an outer-balloon 8 and an inner-balloon 9. The outer-balloon 8 has an outer-balloon-fill port 15. The outer-balloon-fill port 15 can be positioned at any suitable location outside of the inner-balloon 9, such as being desirably positioned at a location near the proximal end of the outer-balloon 8. Furthermore, the inner-balloon 9 can also have an inner-balloon-fill port 11. The two fill ports (11,15) allow medical personnel to control the individual balloon sizes. This can provide a relatively maximum amount of control for the medical personnel to distribute the optimal radiation dose to a patient.

In embodiments of devices and methods, either of the balloon walls of the outer-balloon 8 and/or the inner-balloon 9 can include, but are not limited to, a polymer, such as a biocompatible polymer, desirably a radiation-resistant polymer. Other suitable polymers can include polyolefins such as polyethylene and polypropylene, polyurethanes, polyester, polyvinylchloride, polystyrene, thermoplastic polymers such as C-Flex® (consolidated Polymer Technologies, Inc., Clearwater Fla. 33762), block polymers such as Kraton™ (Kraton Polymers, Houston Tex. 77208), an ionomer such as Surlyn® (Dupont, Wilmington Del. 19880), nylon, latex rubber, and silicon rubber (e.g. SILASTIC™, Dow Corning, Midland, Mich.). Furthermore, the inner-balloon 9 is shown as being disposed on or positioned in association with four treatment catheters 12, 13, 16 and 17, which can also be referred to as radiation-tubes. However it should be noted that the design could use a greater or lesser number of treatment catheters, as can depend on the use of application, and should not construed in a limiting sense.

For illustration purposes, FIG. 2A displays a top-radiation-tube 12 and a bottom-radiation-tube 13. The radiation-tubes 12 and 13 can be positioned on the outside of the inner-balloon 9. However, for future modification, the radiation-tubes 12 and 13, and also radiation-tubes 16 and 17 described below, can also be inserted inside the inner-balloon 9. However, inserting the radiation-tubes 12, 13, 16 and 17 into the inner-balloon 9 typically can have a deficiency, as described above. A device having features of the embodiments can further include multiple, or a plurality of radiation-tubes, such as radiation-tubes 12, 13, 16 and 17. The multiple radiation-tubes, such as radiation-tubes 12, 13, 16 and 17 can be provided in various different shapes, as can depend on the use or application, and should not be construed in a limiting sense. For example, shapes, such as a whisk, or a helix, can be used, such as where the radiation-tubes 12, 13, 16 and 17 are shaped in a circle form around the shaft, such as a central shaft 26. Further, the radiation-tubes 12, 13, 16 and 17 can be configured to run longitudinally along the central shaft 26.

During inflation of the balloon assemblies, such as the outer-balloon 8 and the inner-balloon 9, the radiation-tubes 12, 13, 16 and 17 can expand in a direction perpendicular or substantially perpendicular to the shaft, such as the central shaft 26, while being spaced substantially equal from each other, so to form a three-dimensional catheter framework (or catheter assembly) for the balloon assemblies of embodiments of the double-balloon brachytherapy catheter 1A. The catheter framework can be uniform or substantially uniform in size or regular in shape, such as a spherical, cylindrical or an elliptical shape, as well as can be non-uniform and irregular in shape. A central catheter can also be inserted into the middle of the inner balloon assembly, such as the inner-balloon 9, or the catheter framework. During a radiation therapy procedure, the radiation sources can be inserted into one or more of radiation-tubes 12, 13, 16 and 17 following insertion into a body cavity. The radiation source can be, for example, a solid or a liquid and can be advanced within radiation-tubes 12, 13, 16 and 17 by a fluid or other suitable mechanism, such as a wire, to one or more desired positions within a given radiation tube.

Embodiments of the double-balloon brachytherapy catheter 1A devices can be configured to deliver selective dosages of radiation treatments to different tissue surrounding a body cavity based on the medical treatment needs of a patient. Referring now to FIGS. 2A and 2B, an A-A view of the double-balloon brachytherapy catheter 1A of FIG. 2A is illustrated in FIG. 2B. The A-A view of FIG. 2B illustrates a cross section of the double-balloon brachytherapy catheter 1A of FIG. 2A. For demonstrative purposes, the double-balloon brachytherapy catheter 1A of FIG. 2A has four radiation-tubes. However, embodiments of the double-balloon brachytherapy catheter 1A are not limited in this regard, and embodiments of the double-balloon brachytherapy catheter 1A can have any of a various number of radiation-tubes, similar to the radiation-tubes 12, 13, 16 and 17, as can be more or less in number, and should not be construed in a limiting sense. The A-A view of FIG. 2B illustrates the side-radiation-tube 16, the side-radiation-tube 17, the top-radiation-tube 12, the bottom-radiation-tube 13, a central radiation tube or measurement center 14, and a suction/vacuum-tube 18. The central radiation tube 14 can also allow medical personnel to insert a Metal-Oxide-Semiconductor Field-Effect Transistor (MOSFET) type measurement device or linear array type measurement device to measure the radiation dose that is given to the patient, for example.

FIG. 3A, FIG. 3B and FIG. 3C show the internal structure of the central shaft 26 in an embodiment of the double-balloon brachytherapy catheter 1A with the suction/vacuum-tube 18. FIG. 3A shows the top view of the double-balloon brachytherapy catheter 1A with the suction/vacuum-tube 18. The highlighted area shows the side-radiation-tube 16 and the side-radiation-tube 17 with the suction/vacuum-tube 18. The suction/vacuum-tube 18 is placed outside the outer-balloon 8 and is connected to a distal end cap 10 that forms a distal-tip of the double-balloon brachytherapy catheter 1A. The distal end cap 10 allows for the release of the suction/vacuum-tube 18 during the procedure or after the procedure. The suction/vacuum-tube 18 is removed by medical personnel, such as by pulling out the suction/vacuum-tube 18 separately from the double-balloon brachytherapy catheter 1A, for example.

FIG. 3B shows a side view taken along the section line B-B of FIG. 3C of the double-balloon brachytherapy catheter 1A with the suction/vacuum-tube 18. The suction/vacuum-tube 18 contains small holes or apertures 18a along the suction/vacuum-tube 18. The suction/vacuum-tube 18 allows for removal of fluid or air in the body while the procedure is being performed, and can further provide that the surrounding skin, such as in a body cavity, is pulled relatively tightly against the outer-balloon 8. For illustration purposes, the suction/vacuum-tube 18 is positioned on the outside of the outer-balloon 8. The top-radiation-tube 12, the bottom-radiation-tube 13, and the two side-radiation tubes 16 and 17 are located on the outside of the inner-balloon 9 and within the outer-balloon 8, for example. By utilizing the suction/vacuum-tube 18 and inflating the inner-balloon 9 to position or move the radiation-tubes 12, 13, 16 and 17 away from the central shaft 26, the dose distribution from the radiation source(s) can be significantly improved to provide an optimal treatment plan for the patient. An optimized distribution or optimal treatment is possible by allowing the inner-balloon 9 to selectively change an angle and a length or a location and an angle, or selectively change any one or combination of an angle, length, location, or position of the radiation-tubes 12, 13, 16 and 17. FIG. 3C and the B-B cross-section view illustrated in FIG. 3B, as viewed with the illustration in FIG. 6, illustrate that an inner-balloon-filler 21, that includes an inner-balloon-fill port 11, and an outer-balloon-filler 22, that includes an outer-balloon-fill port 15, are typically located in or associated with a central structure, such as the central shaft 26, of the double-balloon brachytherapy catheter 1A, for example. Furthermore, the B-B view of FIG. 3B and FIG. 3C illustrate the side-radiation-tube 16, the top-radiation-tube 12, the bottom-radiation-tube 13, the side-radiation-tube 17, the suction/vacuum-tube 18, as can be arranged in embodiments of the double-balloon brachytherapy catheter 1A, for example, but should not be construed in a limiting sense, as other suitable arrangements are possible, as can depend on the use or application.

FIGS. 4A and 4B show the internal structure of the double-balloon 8, 9 and a cross-section view of the expansion of the inner-balloon 9 that can selectively change an angle and a length or a location and an angle, or selectively change any one or combination of an angle, length, location, or position of the radiation-tubes 12, 13, 16 and 17 when the inner-balloon 9 is selectively inflated and deflated to optimize radiation delivery. The outer-balloon 8 includes a pair of outer-balloon-locks 24a and 24b, which outer-balloon-locks 24a and 24b can also be mini inner and outer rings and/or adhesive seals or heat seals, positioned at opposite ends of the outer-balloon 8 to provide a vacuum enclosure for the outer-balloon 8. Further, the inner-balloon 9 includes a pair of inner-balloon-locks 25a and 25b, which inner-balloon-locks 25a and 25b can also be mini inner and outer rings and/or adhesive seals or heat seals. The inner-balloon-locks 25a and 25b can be positioned at opposite ends of the inner-balloon 9 to provide a vacuum enclosure or seal for the inner-balloon 9. The C-C view of FIG. 4B of an embodiment of the double-balloon brachytherapy catheter 1A shows the radiation-tubes 12, 13, 16 and 17, but the number of radiation-tubes is not limited in this regard, as can depend on the use or application, for example.

As the inner-balloon 9 is selectively filled, the radiation-tubes 12, 13, 16 and 17 begin to move proportional or according to the increase or decrease in the size of the inner-balloon 9. The inner-balloon 9 expansion volume can vary depending on the fill volume of the outer-balloon 8. The change in the size, length and angle of the radiation-tubes 12, 13, 16 and 17 can allow for a more optimized dose distribution to the patient. The angle measurements of the radiation-tubes 12, 13, 16 and 17 can be calculated or determined depending on the amount of fluid or air inserted into the inner-balloon 9. This can allow for medical personnel to provide a treatment plan that can optimize radiation dose homogeneity and conformality according to the patient's anatomy, for example.

In the radiation-tubes, a fluid radiation source can be any solution of radionuclide(s), e.g., a solution of I-125 or I-131. A radioactive fluid can also be produced from a slurry of a suitable fluid containing small particles of a solid radionuclide, such as Au-198 or Y-90. Moreover, the radionuclide(s) can be embodied in a gel. One radioactive material useful is Iotrex™, a sterile single use, non-pyrogenic solution containing sodium 3-($^{125}$I) iodo-4-hydroxybenzenesulfonate ($^{125}$I-HBS), available from Proxima Therapeutics, Inc. of Alpharetta, Ga.

Figure 5:
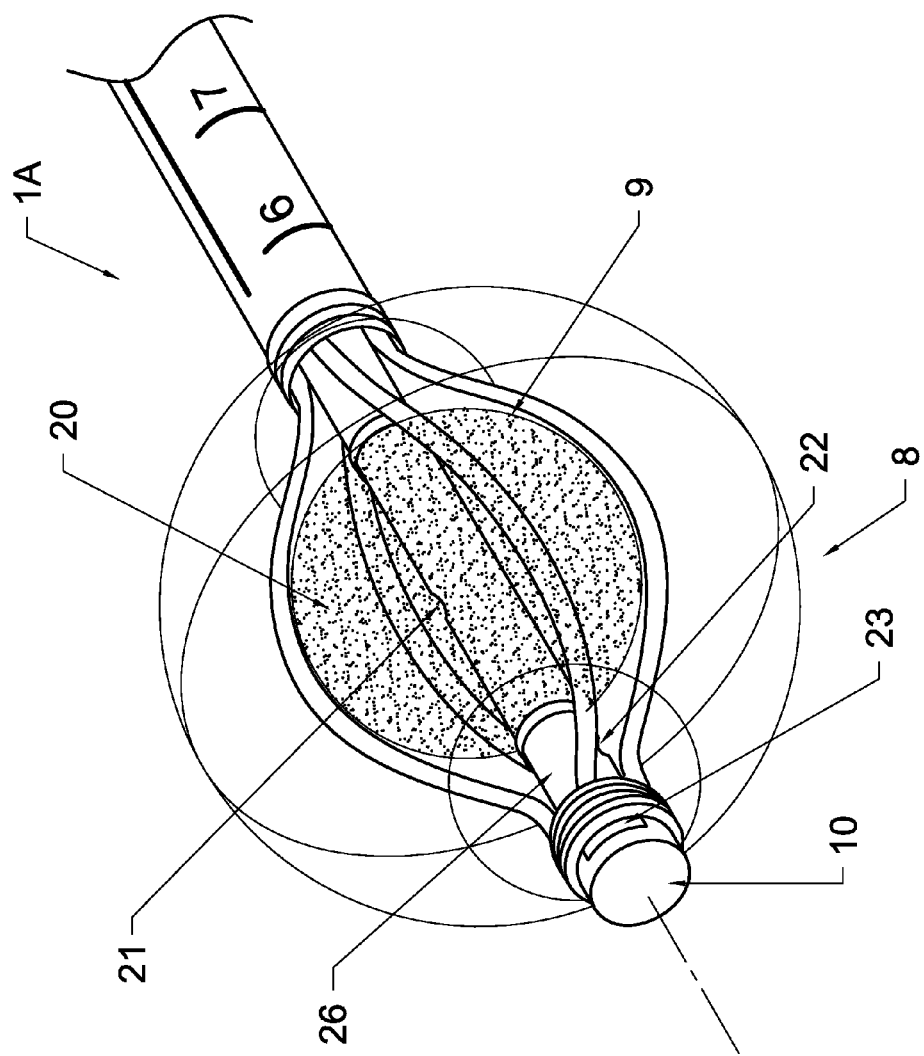
FIG. 5 is a perspective view of an internal balloon fill volume of a double-balloon brachytherapy catheter according to the present invention.

FIG. 5 shows the internal balloon fill volume 20 of the inner-balloon 9 to demonstrate the flexibility of the radiation tubes, such as the radiation-tubes 12, 13, 16 and 17. The inner-balloon 9 is filled using the inner-balloon-filler 21. The inner-balloon 9 can be filled with air or a liquid substance, such as a saline solution or some type of radiation active liquid, for example. The outer-balloon-filler 22 is located outside of the inner-balloon 9 on or in proximity to the central shaft 26, since the outer-balloon-filler 22 fills the entire outer-balloon 8. The outer-balloon 8 can similarly be filled with air or a liquid substance, such as a saline solution or some type of radiation active liquid, for example. The close up view of FIG. 5 of the double balloon 8, 9 of the double-balloon brachytherapy catheter 1A shows schematically the internal components of the balloons 8 and 9.

FIG. 6 shows the internal balloon fill volume 20 with an outer-suction/vacuum-tube 38 on the outer-balloon 8. The outer-suction/vacuum-tube 38 is used to remove fluids and air once the double-balloon brachytherapy catheter 1A is placed in a cavity, such as body cavity. The outer-suction/vacuum-tube 38 can conform to the shape of the outer-balloon 8. For additional functionality, the outer-suction/vacuum-tube 38 can be removed by the medical personnel by pulling on the outer-suction/vacuum-tube 38, thus, allowing removal during or following the placement procedure. The outer-suction/vacuum-tube 38 can be attached to the outer-balloon 8 if desired by medical personnel, but the outer-suction/vacuum-tube 38 is not limited to being attached to the outer-balloon 8. In another embodiment of the double-balloon brachytherapy catheter 1A, the outer-suction/vacuum-tube 38 is not attached to the outer-balloon 8, and the attachment or placement of the outer-suction/vacuum-tube 38 in relation to the outer-balloon 8 should not be construed in a limiting sense, as can depend on the use or application, for example.

FIG. 7A and FIG. 7B show the top and side views of the suction/vacuum-tube 18 relative to an embodiment of the double-balloon brachytherapy catheter 1A. FIG. 7A shows the top view of the suction/vacuum-tube 18, which can be an outer-vacuum-tube, such as the outer-suction/vacuum-tube 38. The suction/vacuum-tube 18 has holes or apertures 18a along the suction/vacuum-tube 18 to remove fluids or air that may be in a cavity, such as a body cavity, in which the double-balloon brachytherapy catheter 1A is positioned for delivery of a radiation treatment. The suction/vacuum-tube 18 can permit or assist in positioning the outer-balloon 8 relatively close to the human skin or tissue, as can be possible. The suction/vacuum-tube 18 is then connected to the end cap 10 of the double-balloon brachytherapy catheter 1A. FIG. 7B shows the side view of the double-balloon brachytherapy catheter 1A with the suction/vacuum-tube 18.

The inner-balloon-locks 25a and 25b create a seal for the inner-balloon 9. The inner-balloon 9 can be selectively inflated or deflated without selective inflation or deflation of the outer-balloon 8, as can be necessary when the double-balloon 8,9 is positioned in relatively small cavities or where an increase in volume by the outer-balloon 8 can possibly damage or rupture some of the internal tissue. The suction/vacuum-tube 18 is connected to the end cap 10 of the double-balloon brachytherapy catheter 1A. The suction/vacuum-tube 18 can be released from the end cap 10 by a suitable release mechanism, such as by operating a mechanical lever or button 23, by the medical personnel to release the suction/vacuum-tube 18 from engagement with the double-balloon brachytherapy catheter 1A. An example of the mechanical lever or button 23 is illustrated in FIGS. 5-6.

Figure 8:
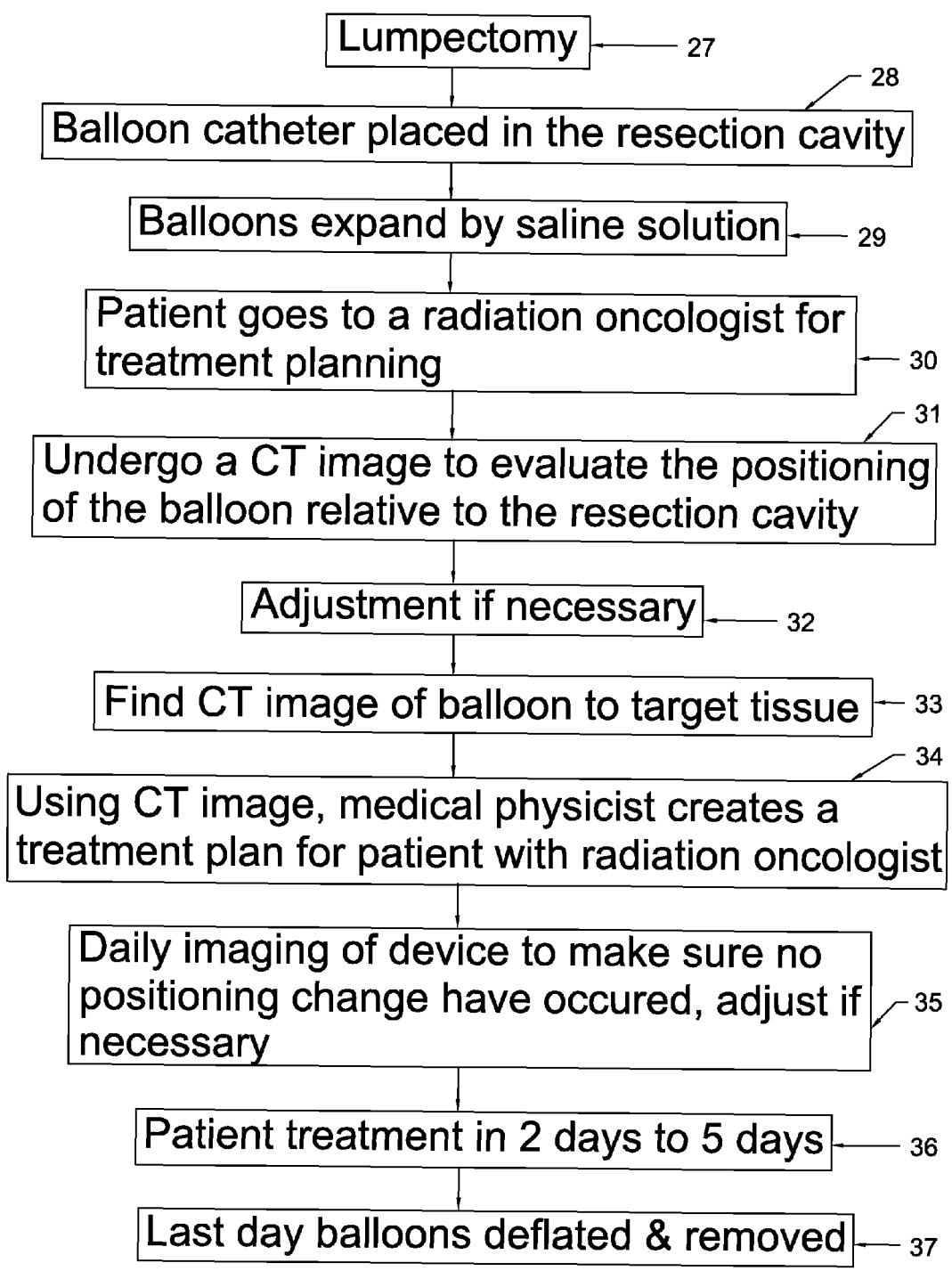
FIG. 8 is a flowchart of a method for treating a patient by a lumpectomy procedure according to the present invention.

FIG. 8 shows a general procedure for a lumpectomy and how to use the double-balloon device, such as the double-balloon brachytherapy catheter 1A. Lumpectomy step 27 is the removal of the breast tumor and some of the normal surrounding tissue. Lumpectomy is a form of "breast-conserving" or "breast preservation" surgery. There are several names used for breast-conserving surgery: biopsy, lumpectomy, partial mastectomy, re-excision, quadrantectomy, or wedge resection, for example. Technically, a lumpectomy is a partial mastectomy, because part of the breast tissue is removed. The catheter, such as the double-balloon brachytherapy catheter 1A, is initially provided deflated to provide for a minimal diameter to allow for insertion through a small incision in the breast. After a few days or weeks following the removal of the tumor, the double-balloon brachytherapy catheter 1A is placed in the resection cavity, as described in step 28. In step 29, both the outer-balloon 8 and the inner-balloon 9 of the double-balloon brachytherapy catheter 1A are expanded.

To evaluate the satisfactory deployment and positioning of the double-balloon brachytherapy catheter 1A device, the patient will typically undergo an imaging procedure, such as an MRI or CT, usually performed by a radiation oncologist. Depending on the tumor area, the medical personnel can selectively inflate or deflate the outer-balloon 8 or the inner-balloon 9. If the area removed is large, the medical personnel may want to inflate the outer-balloon 8 first; thus, allowing for internal structural support. On the other hand, if the area is small, the medical personnel may want to inflate the inner-balloon 9 first to allow the radiation-tubes 12, 13, 16 and 17 to be a certain size and thereafter inflate the outer-balloon 8. Further, the outer-balloon 8 can have grooves along the outer wall. This can allow tissue to seep into the grooves on the outer-balloon wall and can restrict or minimize rotation of the outer-balloon 8 inside the patient, such as when in a cavity.

Once the double-balloon brachytherapy catheter 1A device is fixed or positioned, the patient goes to a radiation oncologist for treatment planning in step 30. The treatment plan typically will be determined by the radiation oncologist. During this time, the patient will be undergoing a CT or MRI image to evaluate the positioning of the outer-balloon 8 relative to the resection cavity, as detailed in step 31. The images can allow the medical personnel to make changes or modify the position of the double-balloon brachytherapy catheter 1A as described in step 32 by adjusting at least one of the outer-balloon 8 or the inner balloon 9, if necessary. In step 33, the double-balloon brachytherapy catheter 1A is placed in an optimal position inside the human cavity by finding a CT image of the balloon to target tissue. In step 34, a medical physicist can create a treatment plan for the patient with the radiation oncologist prescribing the radiation dose by using the CT image from step 33.

The radiation treatment can vary depending on the cavity location relative to other sensitive critical structures. The double-balloon brachytherapy catheter 1A typically will remain in the patient for the entire course of treatment. As described in step 35, during the course of treatment, the patient may receive daily imaging of the double-balloon brachytherapy catheter 1A device to make sure no device positioning changes have occurred relative to the original image which was used to plan the treatment for the case. If changes have occurred, adjustments can be made, if necessary, as a part of step 35. On average, a patient will receive a fractionated treatment typically 2 fractions per day over two to five days of treatment, for one to four hours a day, as illustrated in step 36. During the last day, the outer-balloon 8 and the inner-balloon 9 are deflated to remove the fluid substance or air therein and then the double-balloon brachytherapy catheter 1A device is extracted from the cavity in step 37.

Figure 9:
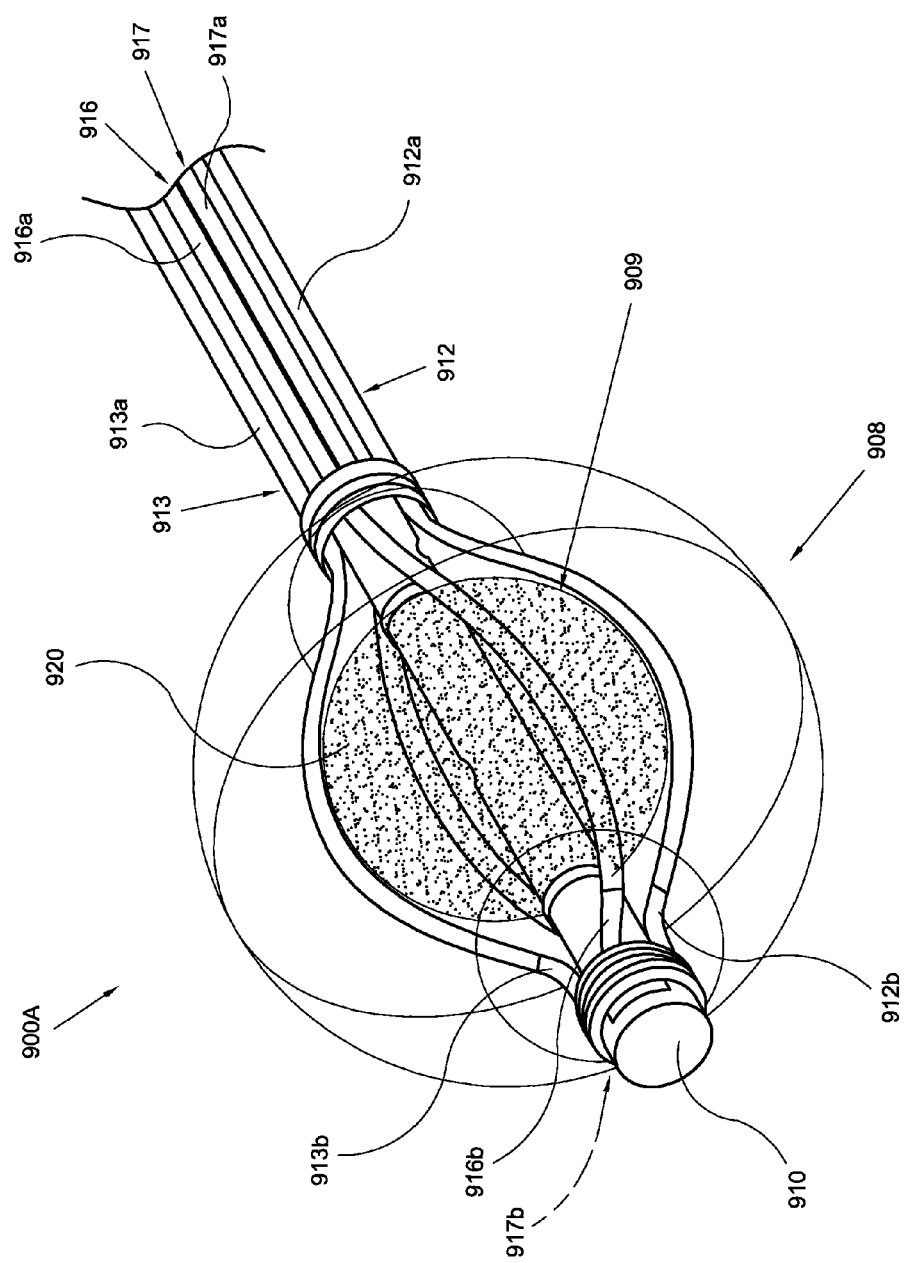
FIG. 9 is a perspective view of a double-balloon brachytherapy catheter having segmented radiation-tubes with a biasing segment according to the present invention.

Referring to FIG. 9, an alternative embodiment of a double-balloon brachytherapy catheter 900A is shown. Similar to the double-balloon brachytherapy catheter 1A of FIGS. 2-7, the double-balloon brachytherapy catheter 900A includes an outer-balloon 908 and an inner-balloon 909. The inner-balloon 909 can have an internal balloon fill volume 920, similar to the internal balloon fill volume 20 of the double-balloon brachytherapy catheter 1A. The double-balloon brachytherapy catheter 900A also includes an end cap 910, similar to the distal end cap 10, with the end cap 910 allowing for the release of a suction-tube during the procedure or after the procedure, such as a lumpectomy procedure.

Continuing with reference to FIG. 9, a plurality of radiation-tubes, such as a first radiation-tube 912, a second radiation-tube 913, a third radiation-tube 916, and a fourth radiation-tube 917 are included with an embodiment of a double-balloon brachytherapy catheter 900A. The plurality of radiation-tubes 912, 913, 916, and 917 are similar to the radiation-tubes 12, 13, 16, 17 of the double-balloon brachytherapy catheter 1A in that they can be filled with a radioactive material used to treat unhealthy tissue. The radioactive material can come in a number of arrangements. For example, the radioactive material can be a high dose rate source. Further, this high dose rate source can be a sealed source, meaning that the source is contained. Examples of isotopes that can be used as the radioactive material include Iridium-192 (symbol $^{192}$Ir), Cobalt-60 (symbol $^{60}$Co), and Ytterbium-192 (symbol $^{169}$Yb).

The plurality of radiation-tubes 912, 913, 916, and 917, just like the radiation-tubes 12, 13, 16, 17, can be disposed on or positioned in association with and moved into a radiation-delivery position by the inner-balloon 909. Further, to optimize radiation delivery by the plurality of radiation-tubes 912, 913, 916, and 917, the size of the outer-balloon 908 and the size of the inner-balloon 909 are mutually independent such that the size of the outer-balloon 908 and the size of the inner-balloon 909 are selectively adjusted independent of each other so that the radiation-delivery position is varied by the size of the inner-balloon 909 to optimize radiation delivery. The plurality of radiation-tubes 912, 913, 916, and 917 can differ from the radiation-tubes 12, 13, 16, and 17 in that each radiation-tube 912, 913, 916, and 917 can be segmented and longitudinally arranged into segments of differing hardness, such as illustrated in FIG. 9. As shown in FIG. 9, the plurality of radiation-tubes 912, 913, 916, and 917 are segmented into segments 912a and 912b, 913a and 913b, 916a and 916b, and 917a and 917b, the segment 917b being indicated by the arrowed line in the view of FIG. 9.

Segments 912a, 913a, 916a, and 917a have a hardness value, such as a durometer value defined on a durometer scale, which can be greater than segments 912b, 913b, 916b, and 917b. In an embodiment, the segments 912b, 913b, 916b, and 917b are biasing segments so that they have spring-like properties. Therefore, when the plurality of radiation-tubes 912, 913, 916, and 917 are disposed on or positioned in association with and moved into a radiation-delivery position by the inner-balloon 909, the biasing segments 912b, 913b, 916b, and 917b will flex and have their inner diameters narrowed as they are being flexed so as to selectively increase or decrease in length. This flexing and adjustment in length can also include a selective change in an angle and a length or a selective change in a location and an angle, or a selective change in any one or combination of an angle, length, location, or position, of the segments of the corresponding radiation-tube 912, 913, 916, and 917, and such flexing and adjustment can establish a more precise radiation-delivery position by or in addition to the selective filling of the inner-balloon 909.

The narrowing of the inner diameters of segments 912b, 913b, 916b, and 917b is such that a diameter is still maintained that allows for the radioactive material, such as Iridium-192, to be positioned within each radiation-tube 912, 913, 916, and 917, and also to be further positioned within each segment 912a, 912b, 913a, 913b, 916a, 916b, 917a, and 917b. Therefore, the inner diameter of segments 912b, 913b, 916b, and 917b will not inhibit or substantially inhibit the movement of the radioactive material with respect to the plurality of radiation-tubes 912, 913, 916, and 917 during treatment.

Additionally, segments 912b, 913b, 916b, and 917b can be made from or include an elastic material. For example, the elastic material can be a silicon material, a silicon spring, or a rubber material, among others. Further, segments 912a, 913a, 916a, and 917a and segments 912b, 913b, 916b, and 917b of the radiation-tubes 912, 913, 916, and 917 can be connected to each other in various forms. For example, the segments can be connected by a heat seal, an adhesive, or various mechanical fasteners, among other examples. It should also be noted in addition to the plurality of radiation-tubes 912, 913, 916, and 917, there can also be a central radiation tube or measurement center, similar to the central radiation tube or measurement center 14 of the double-balloon brachytherapy catheter 1A. This central radiation tube in an embodiment of the double-balloon brachytherapy catheter 900A can allow medical personnel to insert a MOSFET type measurement device or a linear array type measurement device to measure the radiation dose that is given to the patient, for example. This central radiation tube in the embodiment of the double-balloon brachytherapy catheter 900A may or may not be segmented into segments of differing hardness, for example.

Figure 10:
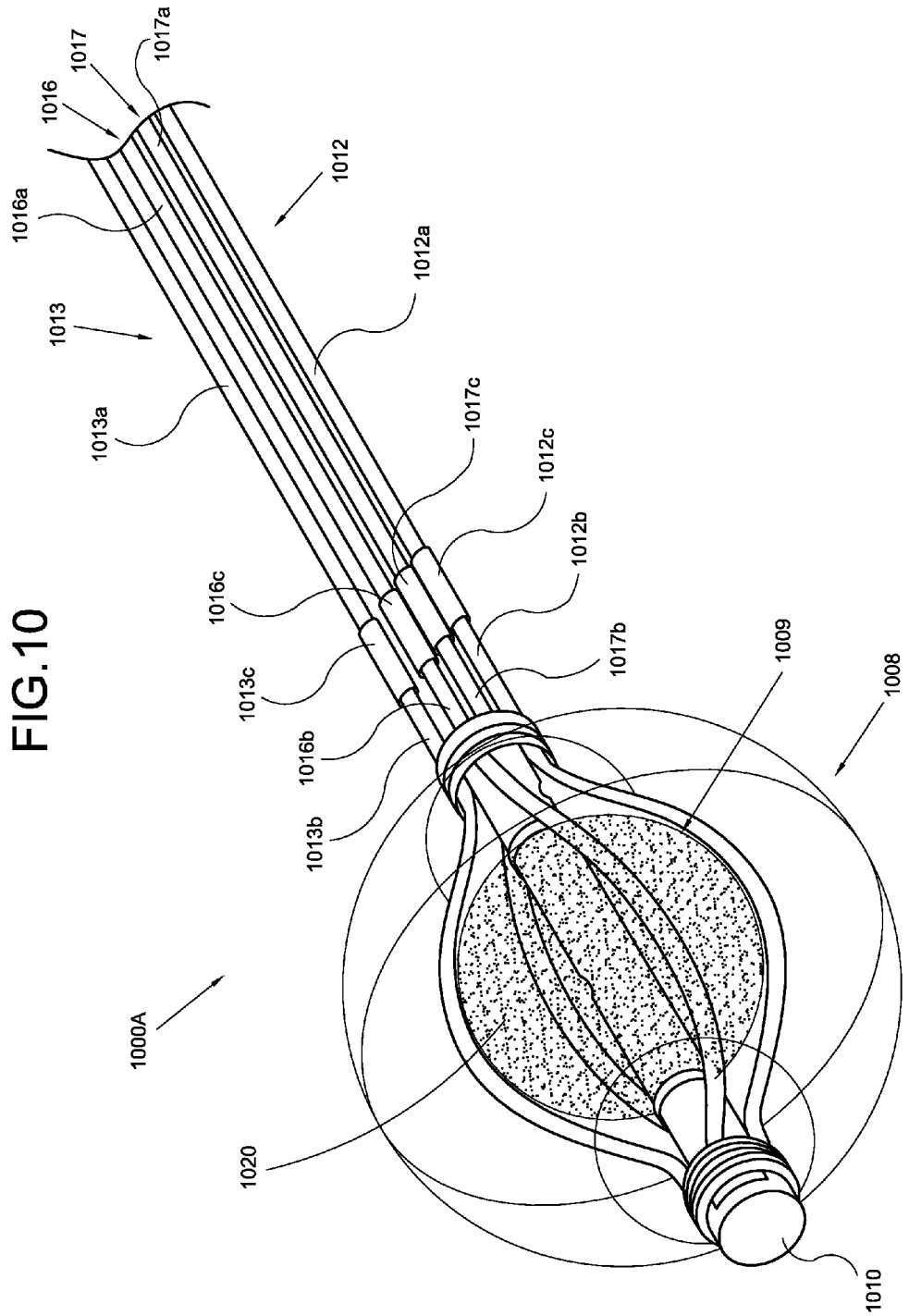
FIG. 10 is a perspective view of a double-balloon brachytherapy catheter having segmented radiation-tubes with a collar securing mechanism according to the present invention.

Referring to FIG. 10, another embodiment of a double-balloon brachytherapy catheter 1000A is shown. Similar to the double-balloon brachytherapy catheter 1A of FIGS. 2-7 and the double-balloon brachytherapy catheter 900A of FIG. 9, the double-balloon brachytherapy catheter 1000A includes an outer-balloon 1008 and an inner-balloon 1009. Just like inner-balloons 9 and 909, inner-balloon 1009 can have an internal balloon fill volume 1020, similar to the internal balloon fill volume 20 and 920. The double-balloon brachytherapy catheter 1000A also includes an end cap 1010, similar to end caps 10 and 910, with the end cap 1010 allowing for the release of a suction-tube during the procedure or after the procedure, similar to that described for the double-balloon brachytherapy catheter 1A, for example.

Continuing with FIG. 10, a plurality of radiation-tubes, such as a first radiation-tube 1012, a second radiation-tube 1013, a third radiation-tube 1016, and a fourth radiation-tube 1017 are included with the double-balloon brachytherapy catheter 1000A. The plurality of radiation-tubes 1012, 1013, 1016, and 1017 are similar to the radiation-tubes 12, 13, 16, 17 and 912, 913, 916, and 917, in that they can be filled with a radioactive material used to treat unhealthy tissue. For example, the radioactive materials Iridium-192, Cobalt-60, and Ytterbium-192 can be used in conjunction with radiation-tubes 1012, 1013, 1016, and 1017. The plurality of radiation-tubes 1012, 1013, 1016, and 1017, just like the radiation-tubes 12, 13, 16, 17, and 912, 913, 916, and 917, can be disposed on or positioned in association with and moved into a radiation-delivery position by the inner-balloon 1009.

The embodiment of the plurality of radiation-tubes 1012, 1013, 1016, and 1017 differs from the radiation-tubes 12, 13, 16, 17 in that each radiation-tube 1012, 1013, 1016, and 1017 is segmented and longitudinally arranged into segments of differing hardness, as discussed herein and illustrated in FIG. 10. Thus, the plurality of radiation-tubes 1012, 1013, 1016, and 1017 are similar to the segmented radiation-tubes 912, 913, 916, and 917. As shown in FIG. 10, the plurality of radiation-tubes 1012, 1013, 1016, and 1017 are segmented into segments 1012a and 1012b, 1013a and 1013b, 1016a and 1016b, and 1017a and 1017b. These various segments can have differing durometer values. For example, segment 1012a can have a durometer value that is higher than the durometer value of segment 1012b. Continuing with this example, radiation-tube 1012 would have segments having different durometer values, such as segments 1012a and 1012b, for example. By having differing durometer values, each radiation-tube 1012, 1013, 1016, and 1017 can have a greater range of flexibility, such as to be able to selectively expand or contract a length of one or more segments to correspond to a radiation delivery position. This flexibility and adjustment in length can also include a selective change in an angle and a length or a selective change in a location and an angle, or a selective change in any one or combination of an angle, length, location, or position of the segments of the corresponding radiation-tube 1012, 1013, 1016, and 1017, and such flexibility and adjustment can establish a more precise radiation-delivery position by or in addition to the selective filling of the inner-balloon 1009. This greater range of flexibility can assist in directing the radiation source to the target tissue.

It should be noted that the radiation-tubes 1012, 1013, 1016, and 1017 can still differ by segments in comparison to the radiation-tubes 912, 913, 916, and 917. For example, in the radiation-tube 912, the segment 912b was elastic in comparison to the segment 912a. Whereas in radiation-tube 1012, segment 1012a does not have to be elastic or as elastic in comparison to segment 1012b, they only need to have differing durometer values, for example. Additionally, the segments 1012a, 1013a, 1016a, and 1017a and the segments 1012b, 1013b, 1016b, and 1017b of the radiation-tubes 1012, 1013, 1016, and 1017 can be connected to each other in various forms. For example, the segments can be connected by heat seal, adhesive, or various mechanical fasteners, among other examples.

As shown in FIG. 10, the segments 1012a, 1013a, 1016a, and 1017a and the segments 1012b, 1013b, 1016b, and 1017b are respectively mechanically fastened to each other by collars, such as a first collar 1012c, a second collar 1013c, a third collar 1016c, and a fourth collar 1017c. The collars 1012c, 1013c, 1016c, and 1017c can have the same or different durometer values than the segments 1012a, 1013a, 1016a, and 1017a and/or the segments 1012b, 1013b, 1016b, and 1017b. Thus, the collars 1012c, 1013c, 1016c, and 1017c can have different hardness values compared to the segments. The collars can be made from various suitable materials, for example from polyether block amide, as can depend on the use or application, and should not be construed in a limiting sense. It should also be noted in addition to the plurality of radiation-tubes 1012, 1013, 1016, and 1017, there can also be a central radiation tube or measurement center, similar to the central radiation tube or measurement center 14 of the double-balloon brachytherapy catheter 1A and the central radiation tube or measurement center of the double-balloon brachytherapy catheter 900A of FIG. 9. This central radiation tube can allow medical personnel to insert a MOSFET type measurement device or linear array type measurement device to measure the radiation dose that is given to the patient. This central radiation tube may or may not be segmented into segments of differing hardness.

A number of exemplary embodiments have been described above. Nevertheless, it will be understood that various modifications may be made. For example, suitable results may be achieved if the described techniques are performed in a different order and/or if components in a described system, architecture, device, or circuit, are combined in a different manner and/or replaced or supplemented by other components or their equivalents. Accordingly, other implementations and other embodiments are within the scope of the following claims.

In embodiments of the double-balloon brachytherapy catheters 1A, 900A and 1000A, the ability to selectively place and position the device and the treatment catheters, such as the radiation tubes, is substantially enhanced over prior balloon devices to optimize the radiation delivery. In embodiments of the double-balloon brachytherapy catheters 1A, 900A and 1000A the outer balloon size and the inner balloon size are mutually independent such that the outer balloon size and the inner balloon size are selectively adjusted independent of each other, and so that the plurality of radiation tubes, such as the radiation tubes 12, 13, 16 and 17 of the double-balloon brachytherapy catheter 1A, the radiation tubes 912, 913, 916 and 917 of the double-balloon brachytherapy catheter 900A, and the radiation tubes 1012, 1013, 1016 and 1017 of the double-balloon brachytherapy catheter 1000A are selectively adjustable by the inner balloon to move into a radiation-delivery position to optimize radiation delivery. For example, in a typical breast radiation therapy procedure, embodiments of the double-balloon brachytherapy catheter can allow the balloon device to be placed through a relatively small incision, approximately one (1) centimeter, so as to allow the outer balloon to be expanded to shape the resection cavity, followed by selectable inflation of the inner balloon to allow placement of the radiation tubes in a position greater than the incision, such as an approximately one (1) centimeter incision, to optimize radiation delivery.

It is to be understood that the present invention is not limited to the embodiments described above, but encompasses any and all embodiments within the scope of the following claims.

I claim:

1. A double-balloon brachytherapy catheter, comprising:
an outer-balloon configured to be filled with a liquid substance or air via an outer-balloon-filler to selectively adjust an outer balloon size;
an inner-balloon configured to be filled with a liquid substance or air via an inner-balloon-filler to selectively adjust an inner balloon size, wherein said inner-balloon is positioned inside said outer-balloon; and
a plurality of radiation-tubes, each radiation-tube being segmented and arranged longitudinally into segments of differing hardness, said plurality of radiation-tubes positioned in association with and moved into a corresponding radiation-delivery position by said inner-balloon, wherein
the outer balloon size and the inner balloon size are mutually independent and selectively adjusted independent of each other, and each radiation-tube of said plurality of radiation-tubes is selectively adjustable to the corresponding radiation-delivery position by varying the inner balloon size to optimize radiation delivery.

2. The double-balloon brachytherapy catheter according to claim 1, wherein
said inner-balloon-filler increases a volume of said inner-balloon to increase a size of said inner-balloon to a corresponding said inner balloon size that provides a corresponding change in an angle and a length of each radiation-tube of said plurality of radiation-tubes.

3. The double-balloon brachytherapy catheter according to claim 1, further comprising:
a vacuum-tube, the vacuum-tube being attached to a distal-tip of said double-balloon brachytherapy catheter to allow for removal of fluids or air from around the distal-tip.

4. The double-balloon brachytherapy catheter according to claim 1, wherein
the segments of differing hardness of each radiation-tube include at least one biasing segment.

5. The double-balloon brachytherapy catheter according to claim 4, wherein
the at least one biasing segment comprises an elastic material.

6. The double-balloon brachytherapy catheter according to claim 5, wherein
the elastic material is silicon or rubber.

7. The double-balloon brachytherapy catheter according to claim 5, wherein
each radiation-tube of said plurality of radiation-tubes is positioned within said outer-balloon and to an outside of said inner-balloon.

8. The double-balloon brachytherapy catheter according to claim 1, wherein
the segments of differing hardness include at least one segment having a lower durometer value than another segment.

9. The double-balloon brachytherapy catheter according to claim 1, wherein
the segments of differing hardness are connected by a securing mechanism.

10. The double-balloon brachytherapy catheter according to claim 9, wherein
the securing mechanism is a collar.

11. A double-balloon brachytherapy catheter, comprising:
an outer-balloon configured to be filled with a liquid substance or air to selectively adjust an outer balloon size;
an inner-balloon configured to be filled with a liquid substance or air to selectively adjust an inner balloon size, wherein said inner-balloon is positioned inside said outer-balloon; and
a plurality of radiation-tubes positioned in association with and moved into a corresponding radiation-delivery position by said inner-balloon, each radiation-tube being segmented and arranged longitudinally into segments of differing hardness, and each radiation-tube configured to selectively expand or contract a length of one or more segments to correspond to the corresponding radiation-delivery position, wherein
said inner-balloon selectively positions each radiation-tube of said plurality of radiation-tubes within said outer-balloon, and the outer balloon size and the inner balloon size are selectively adjusted independent of each other, and each radiation-tube of said plurality of radiation-tubes is selectively adjustable to correspond to the corresponding radiation-delivery position by varying the inner balloon size to optimize radiation delivery by a corresponding radiation source.

12. The double-balloon brachytherapy catheter of claim 11, wherein
a volume of said inner-balloon is selectively adjusted to a corresponding said inner balloon size to selectively expand or contract the length of one or more segments of each radiation-tube of said plurality of radiation-tubes to change an angle and a length of a corresponding radiation-tube of said plurality of radiation-tubes to correspond to the corresponding radiation-delivery position.

13. The double-balloon brachytherapy catheter of claim 11, wherein
a volume of said inner-balloon is selectively adjusted to a corresponding said inner balloon size to selectively expand or contract the length of one or more segments of each radiation-tube of said plurality of radiation-tubes to change a location and an angle of a corresponding radiation-tube of said plurality of radiation-tubes to correspond to the corresponding radiation-delivery position.

14. The double-balloon brachytherapy catheter of claim 11, further comprising:
a vacuum-tube attached to a distal-tip of said double-balloon brachytherapy catheter to allow for removal of fluid or air from around the distal-tip.

15. The double-balloon brachytherapy catheter of claim 11, further comprising:
a vacuum-tube positioned outside of said outer-balloon to remove fluid or air from a cavity to the outside of said outer-balloon.

16. The double-balloon brachytherapy catheter of claim 11, wherein
each radiation-tube of said plurality of radiation-tubes is positioned within said outer-balloon and to an outside of said inner-balloon.

17. A method for operating a double-balloon brachytherapy catheter, comprising:
filling a liquid substance or air into an outer-balloon via an outer-balloon-filler to selectively adjust and achieve an outer balloon size;
filling a liquid substance or air into an inner-balloon via an inner-balloon-filler to selectively adjust and achieve an inner balloon size, said inner-balloon being positioned inside said outer-balloon;
positioning a plurality of radiation-tubes within said outer-balloon, each radiation-tube of said plurality of radiation-tubes being segmented and arranged longitudinally into segments of differing hardness;
selectively expanding or contracting to a corresponding length one or more of the segments of a corresponding one or more of said plurality of radiation-tubes to correspond to a corresponding radiation-delivery position by selectively filling said inner-balloon via the inner-balloon-filler; and
selectively controlling the outer balloon size and the inner balloon size independently of each other, wherein
the one or more segments of the corresponding one or more of said plurality of radiation-tubes are selectively expanded or contracted to the corresponding length to correspond to the corresponding radiation-delivery position by varying the inner balloon size to optimize radiation delivery.

18. The method for operating a double-balloon brachytherapy catheter of claim 17, further comprising:
loading radioactive material into at least one of said plurality of radiation-tubes to provide a radiation dose treatment.

19. The method for operating a double-balloon brachytherapy catheter of claim 17, further comprising:
selectively increasing or decreasing a volume of said inner-balloon to vary said inner balloon size to selectively expand or contract to the corresponding length one or more segments of the corresponding one or more of said plurality of radiation-tubes to correspond to a change in an angle, a length, a location, a position, or a combination thereof, of a corresponding radiation-tube of the plurality of radiation-tubes to optimize radiation delivery.

20. The method for operating a double-balloon brachytherapy catheter of claim 17, further comprising:
removing by a vacuum-tube fluid or air from a cavity receiving the double-balloon brachytherapy catheter.

21. A double-balloon brachytherapy catheter, comprising:
an outer-balloon configured to be filled with a liquid substance or air via an outer-balloon-filler to selectively adjust an outer balloon size;
an inner-balloon configured to be filled with a liquid substance or air via an inner-balloon-filler to selectively adjust an inner balloon size, wherein said inner-balloon is positioned inside said outer-balloon; and
a plurality of radiation-tubes, each radiation-tube of the plurality of radiation-tubes being segmented and arranged longitudinally into segments of differing hardness, said plurality of radiation-tubes positioned in association with and moved into a corresponding radiation-delivery position by said inner-balloon, wherein
the outer balloon size and the inner balloon size are mutually independent and selectively adjusted independent of each other, and one or more of the segments of one or more of the plurality of radiation tubes are selectively expanded or contracted to correspond to the corresponding radiation-delivery position by varying the inner balloon size to optimize radiation delivery.

* * * * *